United States Patent
Minot et al.

(10) Patent No.: US 9,213,005 B2
(45) Date of Patent: Dec. 15, 2015

(54) X-RAY ANTI-SCATTER GRID

(71) Applicant: Incom, Inc., Charlton, MA (US)

(72) Inventors: Michael J. Minot, Andover, MA (US); Joseph M. Renaud, Brimfield, MA (US); Daniel C. Bennis, Spencer, MA (US); Michael A. Detarando, Fiskdale, MA (US)

(73) Assignee: INCOM, INC., Charlton, MA (US)

( * ) Notice: Subject to any disclaimer, the term of this patent is extended or adjusted under 35 U.S.C. 154(b) by 145 days.

(21) Appl. No.: 14/071,236

(22) Filed: Nov. 4, 2013

(65) Prior Publication Data
US 2015/0124929 A1    May 7, 2015

(51) Int. Cl.
*G21K 1/00* (2006.01)
*G01N 23/04* (2006.01)
*G21K 1/02* (2006.01)

(52) U.S. Cl.
CPC ............. *G01N 23/04* (2013.01); *G21K 1/025* (2013.01)

(58) Field of Classification Search
CPC .................................. G21K 1/10; G01N 23/04
USPC ......................................................... 378/154
See application file for complete search history.

(56) References Cited

U.S. PATENT DOCUMENTS

| 6,678,352 B1 * | 1/2004 | Kumakhov .................... 378/154 |
| 8,989,353 B2 * | 3/2015 | Kaneko ........................ 378/154 |
| 2002/0176538 A1 * | 11/2002 | Wimberger-Friedl et al. ............................. 378/154 |
| 2004/0251420 A1 * | 12/2004 | Sun .......................... 250/370.09 |

* cited by examiner

*Primary Examiner* — Michael Maskell
(74) *Attorney, Agent, or Firm* — BainwoodHuang

(57) ABSTRACT

An X-ray anti-scatter grid having thinner X-ray opaque layers, smaller X-ray opaque diameters, greater aspect ratio, lower weight and improved image resolution is disclosed. A method of forming the X-ray anti-scatter grid is disclosed that includes a set of hollow X-ray transparent glass capillary tubes that are fused together, with an X-ray opaque layer thick enough to block X-rays at a specified energy inside the capillary tubes. The capillary tubes provide the high aspect ratio and light weight, while the X-ray opaque layer is provided by a deposition process that has features similar to atomic layer deposition (ALD). The high aspect ratio and thin layers improves resolution and decreases image artifacts, and large area X-ray anti-scatter grids are provided by aligning the axis of the an X-ray opaque layers to the X-ray source.

24 Claims, 7 Drawing Sheets

X-RAY ANTI-SCATTER GRID

BACKGROUND

X-rays are commonly used in medical and dental imaging techniques for examining living things, as well as in internal examination of objects in materials analysis and other fields. X-rays are commonly passed through the object to be imaged, such as a person or a metal casting, and the X-rays that are not absorbed and pass through the object are recorded on a medium, such as a photographic film or a semiconductor detector.

X-rays generally travel in straight lines directly between an X-ray source, through the object to be imaged, and to the detector. However, the clarity and resolution of the image may be degraded by X-rays that have a distorted or bent path, due to being scattered or deflected away from the usual straight path rather than simply being absorbed, for example, being scattered by a bone. In this case any particular portion of the X-ray detector will record some X-rays that have not travelled to the detector in a straight line, which will represent a source of 'noise', degrading the signal to noise ratio (S/N) of the image. The 'noise' may reduce the sharpness of the image and result in an image that does not provide a clear view of the features to be imaged.

A method of reducing the number of X-rays that do not travel directly from the X-ray source to the detector includes the use of thin sheets of an X-ray opaque material such as lead, separated by sheets of an X-ray transparent (also referred to as X-ray lucent) material such as aluminum, to form a structure similar to a Venetian Blind. This structure reduces the number of X-rays that travel to the detector with greater than a specific blocking angle to the vertical lead sheets, where the blocking angle is determined by a ratio between the height (or depth D) of the vertical lead sheets and the separation (L) between the vertical sheets (i.e., an L/D ratio). The thickness of the lead sheets must also be great enough to block X-rays of the energy level being used.

It is to be understood that since the lead/aluminum sheet method uses lead sheets to form a linear array, the blocking angle is only applicable in the direction perpendicular to the linear array, and that it would require a second such linear array placed on top of the first, and rotated ninety degrees relative to the first linear array, to form a grid pattern to obtain a general X-ray anti-scatter device. In general, the grid is placed somewhere between the object to be examined and the detector.

SUMMARY

Unfortunately, there are deficiencies with the known methods of reducing the incidence angle of X-rays and blocking X-rays that have been scattered. These deficiencies include excess weight and cost, decreased durability, increased X-ray dose, and the formation of image artifacts on the detectors due to the anti-scatter grid itself blocking X-rays. For example, in order to obtain a L/D ratio sufficient to block most off-axis X-rays using the lead and aluminum sheet structure discussed above, the height of the lead sheets may need to be fifty times the distance between adjacent lead sheets. Such a structure is difficult to fabricate and greatly increases the weight of the X-ray anti-scatter grid needed to reduce the number of non-vertical X-rays reaching the detector and improving image contrast.

An X-ray anti-scatter device that addresses the problems of the prior art includes an X-ray transparent dielectric material having a set of X-ray opaque tubes, where each of the X-ray opaque tubes has an axial orientation, an outside width and an inside width. In an embodiment the wall thickness of the X-ray opaque tubes is selected to obtain what is known as an X-ray open area ratio of greater than 80%. In an embodiment inside width or diameter of the X-ray opaque tubes and the length of the tubes, as determined by the thickness of the X-ray transparent dielectric material, results in a tube length to width ratio of greater than 100/1, which results in excellent blocking of off-axis X-rays. In an embodiment the X-ray transparent dielectric material is formed of borosilicate glass, which is inexpensive and easy to form into thin strong tubes, and the X-ray opaque tubes are formed of tungsten, which has excellent X-ray stopping power, with the tungsten as a layer inside a hollow capillary tube extending the length of the tube. In an embodiment each X-ray opaque tube is directed towards a point a selected distance away from the dielectric layer with either a curved surface or with a flat plane surface. In an embodiment the dielectric material is formed by a set of connected straight hollow open ended tubes, each tube including a layer of X-ray opaque material covering an inside surface.

A method of forming an X-ray anti-scatter device may include forming a block having a desired shape, such as a rectangular solid, from a set of connected parallel straight hollow capillary tubes made of an X-ray transparent dielectric material, such as glass or plastic. One embodiment forms the block by heat drawing glass tubes into thin walled narrow diameter capillary tubes, and then heat fusing the capillary tubes together in the desired shape. Ensuring that the ends of the capillary tubes are open, and forming a layer of an X-ray opaque material on the inside surface of each one of the capillary tubes.

In an embodiment the X-ray opaque layer may be formed by alternating layers of alumina and tungsten, and the overall composition of the X-ray opaque layer may be varied from the bottom to the top by changing the relative thickness of the alternating layers. The alternating layers may be formed by an atomic layer deposition (ALD) method or a chemical vapor deposition (CVD method or a combination of the two methods. The X-ray opaque layer composition may vary from a composition near the bottom selected for thermal stress relief or coefficient of thermal expansion (CTE) matching with the X-ray transparent dielectric material, to an essentially pure layer of tungsten at the top for maximum X-ray stopping power.

An X-ray imaging system using the anti-scatter device may include an X-ray source, a location for placing an object to be imaged, such as a human patient, the anti-scatter grid, and an X-ray detector and recording system. In an embodiment the X-ray imaging device may include a scintillating material attached to the X-ray anti-scatter device and a solid state imaging device attached to the scintillating material, for an integrated device.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

DETAILED DESCRIPTION

Figure 1:
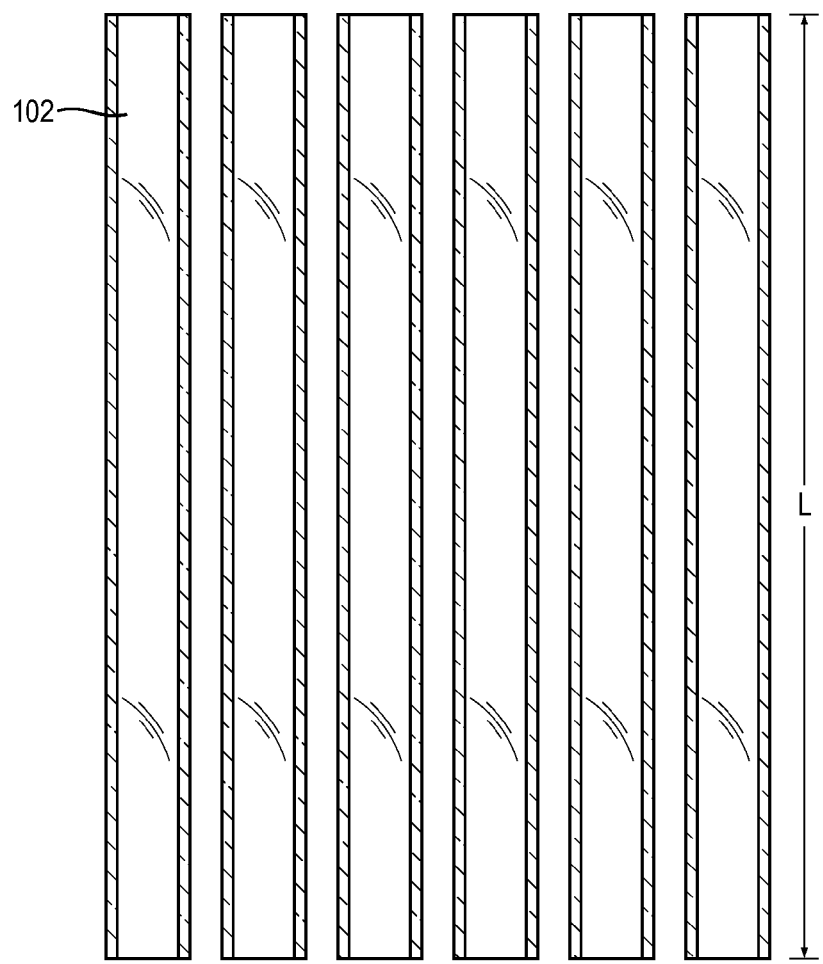
FIG. 1 is a side view of six representative rows of X-ray transparent dielectric tubes aligned in a parallel arrangement prior to forming an attachment, in accordance with an embodiment.

FIG. 1 is a side view of six representative rows of X-ray transparent dielectric tubes 102 aligned in a parallel arrangement prior to forming an attachment, where the gap between the tubes 102 is intended to show that each tube is a separate and unattached tube, such as any sort of glass tube or plastic tube. The gap shown between the tubes 102 may not exist in all situations where, for example, the tubes 102 may be physically bound together by a clamp for handling purposes.

It should be noted that the tubes 102 are formed of materials that are X-ray transparent, and the tubes 102 are not necessarily transparent at visible light wavelengths. The definition of X-ray transparent, as used herein, is a substantial percentage of incident X-rays at a specific X-ray energy will not be absorbed or deflected in the material, and will pass directly through the material thickness. Another substantially equivalent term for X-ray transparent may be X-ray lucent. A thickness of a material may be said to be X-ray transparent if 90% of incident radiation is transmitted, as compared to transmission without the material.

Each X-ray transparent dielectric tube 102 will have a length L that will in part determine the overall thickness of an eventual X-ray transparent dielectric layer. The tubes 102 may be formed by heat drawing standard hollow glass tubes into thinner and longer form, by methods well known in the art, into capillary tubes having a desired diameter and wall thickness. The heat drawing process may be repeated as many times as needed to obtain the diameter required. Smaller diameter tubes may result in X-ray anti-scatter grids having superior image improvement properties. Tubes may also be formed of plastic.

Figure 2:
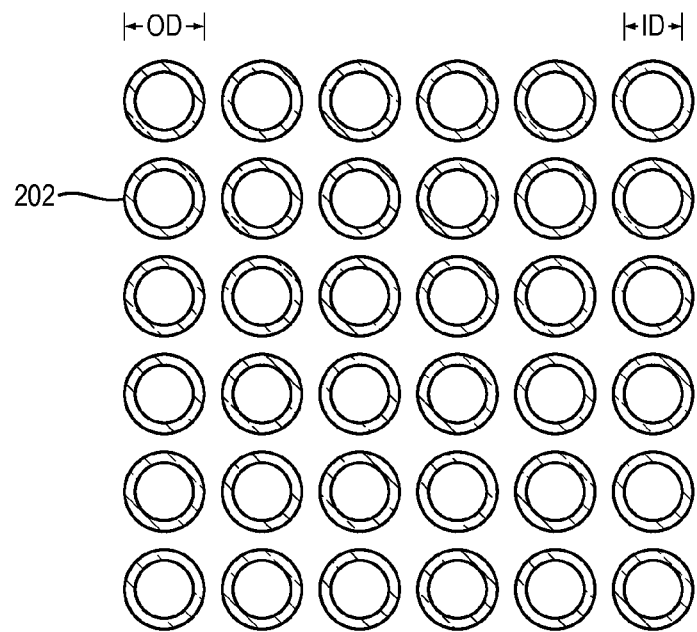
FIG. 2 is top view of the arrangement of the X-ray transparent dielectric tubes of FIG. 1, in accordance with an embodiment.

FIG. 2 is top view of the arrangement of the X-ray transparent dielectric tubes of FIG. 1, showing six rows of six X-ray transparent dielectric material tubes 202 forming a 6×6 matrix of tubes. In general, an anti-scatter grid would comprise thousands of such tubes. The gaps between the tubes 202 again indicate that the individual tubes 202 are not connected to each other. Each tube 202 has an outer diameter OD and an inner diameter ID.

Figure 3:
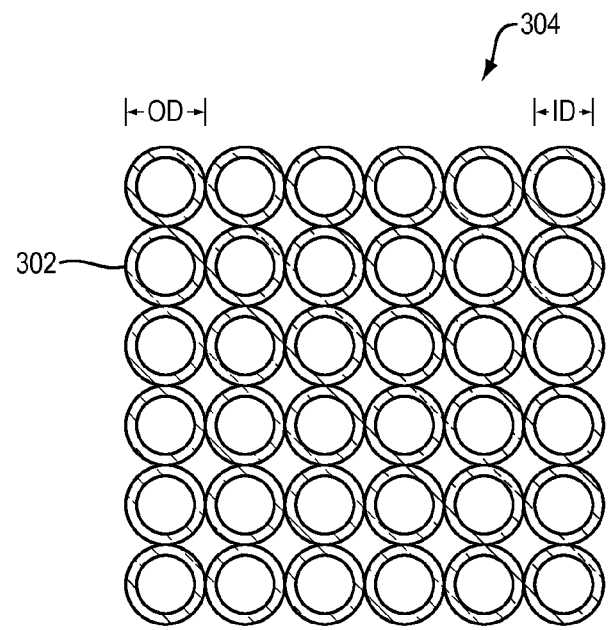
FIG. 3 is a top view of the arrangement of FIG. 2 after a process of attachment, in accordance with an embodiment.

FIG. 3 is a top view of the arrangement of FIG. 2 after a process of attachment, for example heat fusing a bundle of glass capillary tubes 302 into a rectangular block 304 as shown. Any sort of shape may be formed as desired for the eventual device, and not simply the block shown. Further, the arrangement of the tubes may be of a different orientation than the square pack array shown, and may include a denser hexagonal close pack arrangement, or other well known arrays. Since the X-ray transparent tubes 302 have been fused together and attached, there is no longer any gap shown between the individual tubes 302, although there may still be a gap 306 at the intersection of four X-ray transparent tubes, or the shown gap 306 may be filled, or the tube shape altered. The X-ray transparent tubes 302 still have an outer dimension OD and an inner dimension ID, but the cross section of the X-ray transparent tubes may not be circular as shown, but may form a hexagonal array with a circular inside shape, or an oval shape, or other shapes depending upon the process used in forming the X-ray transparent material.

Figure 4:
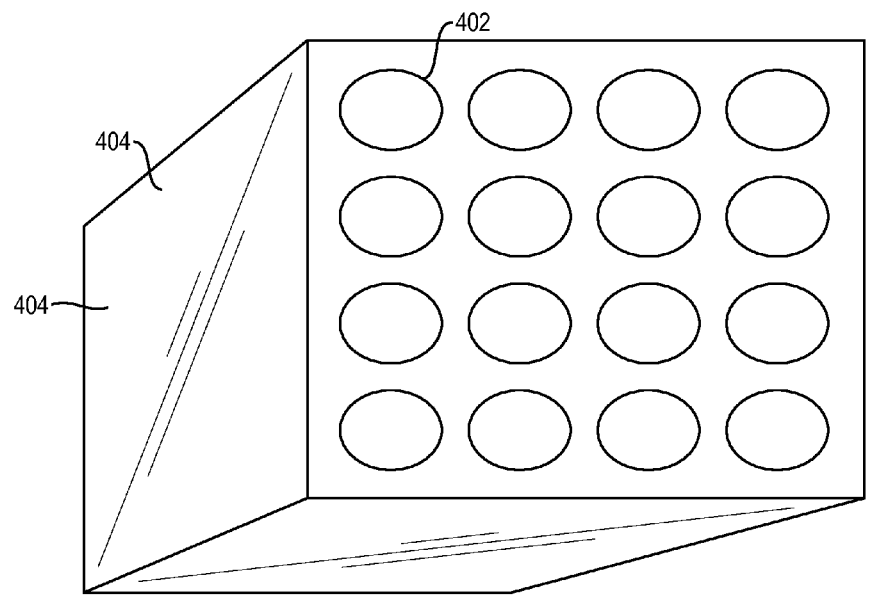
FIG. 4 is a perspective view of the arrangement of FIG. 3, in accordance with an embodiment.

FIG. 4 is a perspective view of the arrangement of FIG. 3, showing the X-ray transparent tubes 302 of FIG. 3 fused together and compressed in one dimension to form an array of oval or elliptical shaped holes 402 in a block of X-ray transparent material 404. The holes 402 are generally cylindrical channels in the X-ray transparent material that traverse the material 404 from the shown front surface to the not shown back surface on the opposite side. The holes 402 do not need to be elliptical as shown and may be circular, or hexagonal or other shapes. It should be noted that the relative sizes and separations of the holes 402 in the figure are to illustrate the formation, and in general the holes 402 will have smaller separation distances than shown.

In the shown embodiment the gaps 306 of FIG. 3 at the intersection of four of the tubes 302 have been filled by the flow of the glass during the fusing process, but this is not necessary and the presence of spaces such as the gaps 306 of FIG. 3 will not affect the X-ray anti-scatter device significantly. In this embodiment the X-ray transparent material 404 has been formed by the fusing of the glass capillary tubes 302 of FIG. 3. A similar type device may be formed using plastic or other materials.

While the described embodiment illustrates a flat micro-channel plate formed of numerous thin tubes, a micro-channel plate may also be formed using other methods. For example, the arrangement of FIG. 4 may be formed by electrochemical oxidation and directional etching in layers of metallic materials or metallic oxide layers, such as anodic aluminum oxide layers.

Figure 5:
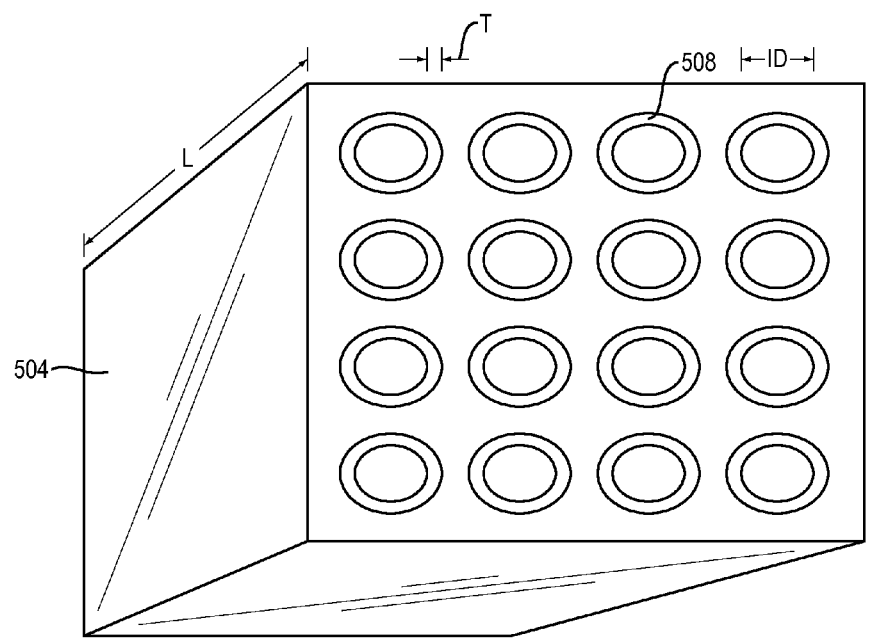
FIG. 5 is a perspective view of the arrangement of FIG. 4 after deposition of an X-ray opaque material, in accordance with an embodiment.

FIG. 5 is a perspective view of the arrangement of FIG. 4 after an X-ray opaque material is deposited on an inside surface of the hole 402 of FIG. 4, where the X-ray opaque material forms a layer 508 that has a thickness T. The thickness T is selected depending upon the material forming the X-ray opaque layer 508, and is selected to be thick enough to substantially absorb all incident X-rays having a specified energy. For example, the X-ray anti-scatter device may be designed to block off-axis X-rays having an energy of 25 KeV, as may be used in mammography procedures, and have the X-ray opaque material layer formed of tungsten (W) having a thickness of 800 nanometers to block 90% of the incident X-rays. If another X-ray blocking material such as lead (Pb) is used, the layer 508 may be thinner or thicker than the comparable tungsten layer. The X-ray opaque layer 508 may extend substantially the entire length L of channel 402 from FIG. 4 in the X-ray transparent material 504, but this may not be required for proper operation of the X-ray anti-scatter device.

The ratio of the length L versus the inner dimension ID of the tube formed by the X-ray opaque layer 508 helps determine the percentage of undesirable off-axis X-rays that will traverse the opaque material and reach the X-ray detector that forms the image. A larger ratio improves the image quality. It should again be noted that in general the spacing between the X-ray opaque layers 508 is smaller than shown in the figures. It should also be noted that the X-ray opaque material layer 508 will not be separated from the x-ray transparent material 504 as shown in the figure. The figure shows a gap in order to make clear that the X-ray opaque layer 508 is different from the X-ray transparent material 504 of the block.

Figure 6:
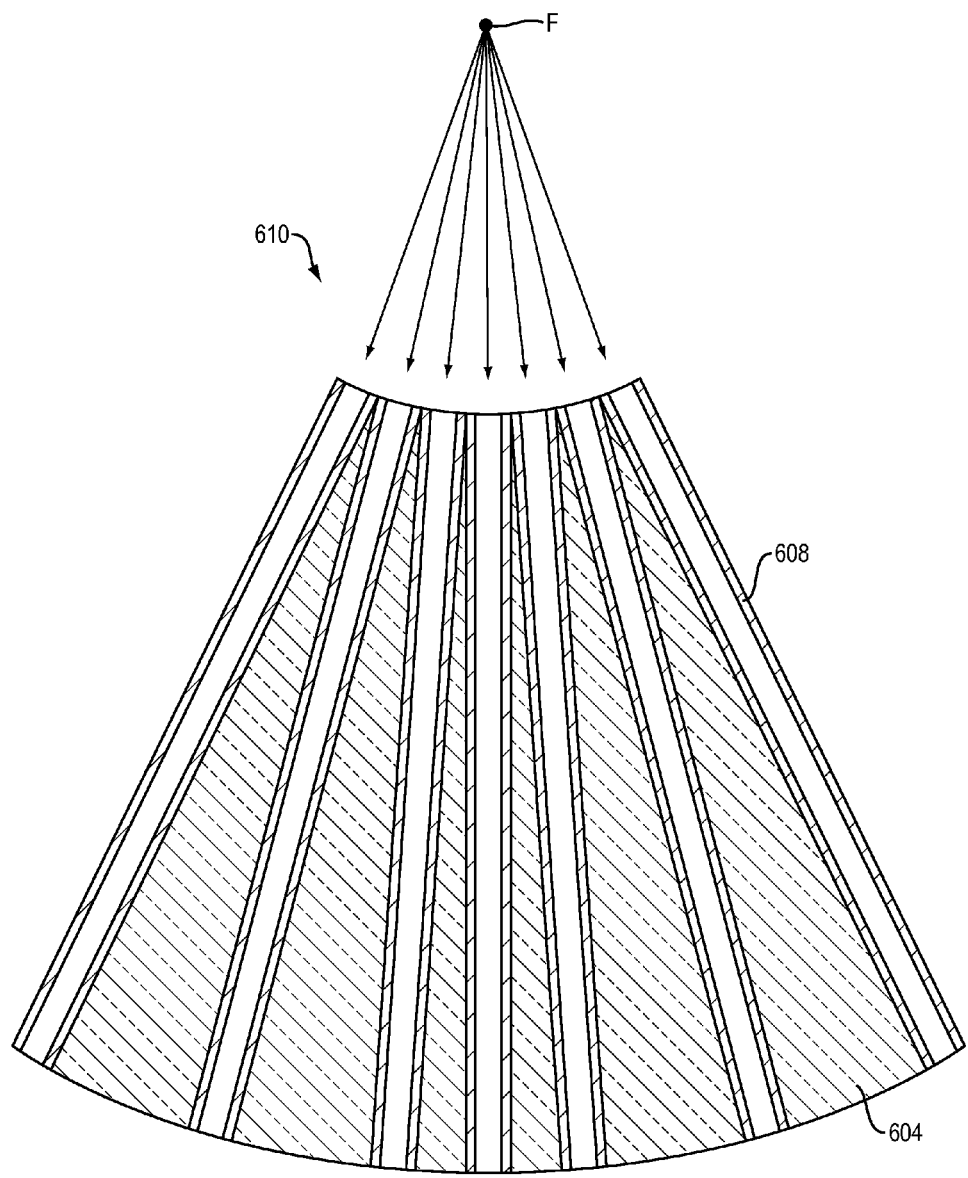
FIG. 6 is a side view of a set of focused X-ray tubes, in accordance with an embodiment.

FIG. 6 is a side view of a set of focused X-ray tubes, in which the X-ray opaque tubes 608 include X-ray transparent channels, for example air, that are each directed towards a focus point F. The point F may represent an X-ray source in an X-ray imaging system. The X-ray opaque tubes 608 may be an X-ray opaque material layer on an X-ray transparent material tube, as shown in FIG. 5, and the X-ray opaque tubes 608 may be separated by an X-ray transparent material 604, which may be formed by fusing the tubes 302 shown in FIG. 3, or by other well-known methods. The X-ray opaque tubes 608 may have a constant diameter as shown, or the forming process may cause the channels in the X-ray transparent material 604 to change in diameter.

The X-ray anti-scatter device shown in the figure has a curved surface 610 formed by the connected open ends of the X-ray opaque tubes 608. The surface 610 may be a concave surface as shown in the figure, but the invention is not necessarily so limited, and many different surface shapes may be used depending upon the application for which the X-ray anti-scatter device is intended. In the case of a point source X-ray generator, such as may be used in mammography or dental X-rays, the illustrated concave shape with the X-ray source at the location F may be a preferred arrangement. The X-ray anti-scatter device shape shown may be difficult to handle, aim and store, which may be addressed with a simple light carrying structure made of organic foam, or other X-ray transparent material, having a cut out portion shaped to match and hold the device shape. The cut out portion may also have an insert placed on top of the X-ray anti-scatter device since the foam is X-ray transparent and will not impact the operation of the X-ray anti-scatter device. Such a foam carrying apparatus may also protect the X-ray anti-scatter device from impacts which may damage the glass tube structure.

Figure 7:
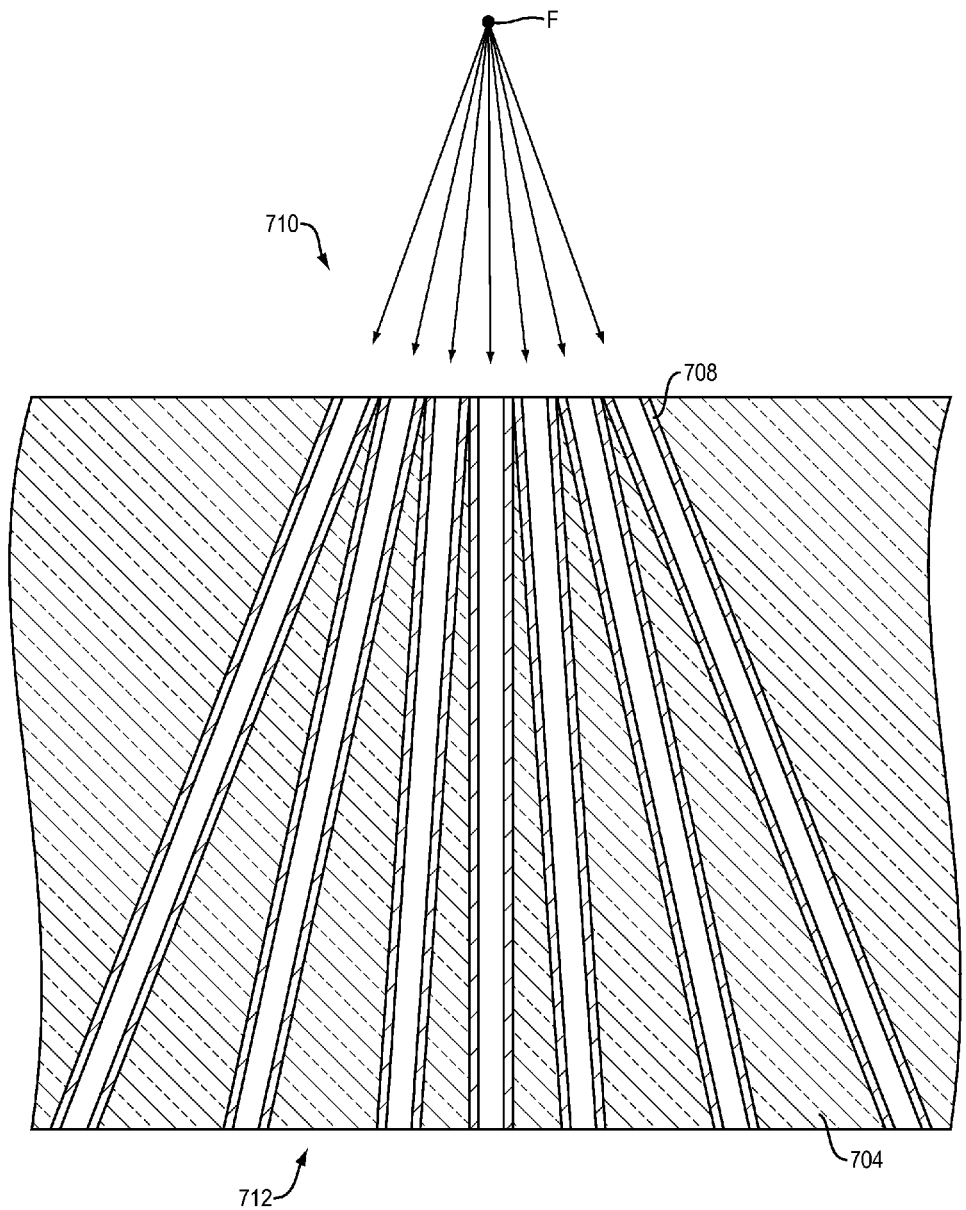
FIG. 7 is another side view of a set of focused X-ray tubes with the tops of the tubes remaining in a plane, in accordance with an embodiment.

FIG. 7 is another side view of a set of focused X-ray tubes with the tops of the X-ray opaque tubes 708 located in a plane formed of the X-ray transparent material 704, with the X-ray opaque tubes 708 each aligned with a focal point F. It should be noted that the open tops of the X-ray opaque tubes 708 do not need to be in physical contact as shown in the figure, but rather may be placed throughout the material 704. Close placement of the X-ray opaque tubes 708 may be desirable to reduce the number of off-axis X-rays that can pass between the X-ray opaque tubes 708, and thus reduce the eventual X-ray image quality. The arrangement shown in FIG. 7 may be preferred over the arrangement shown in FIG. 6 due to what may be considered a more compact and easily handled shape of the X-ray anti-scatter device. The shape of the X-ray anti-scatter device shown in the figure may be obtained by a controlled thermal slumping process on a curved section cut out of a block such as shown in FIG. 5, or thermal slumping of the arrangement of FIG. 6, or by other methods known in the art. Different methods of formation may result in variations in the channel diameter and thus in the configuration of the X-ray opaque tubes 708 and the X-ray transparent material 704 from the features illustrated in FIG. 7.

Figure 8:
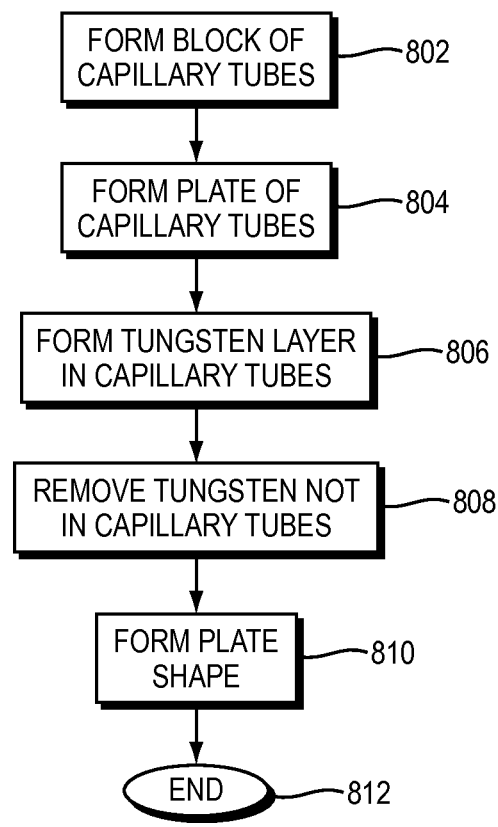
FIG. 8 is a flowchart of a method of forming the arrangement shown in FIG. 5, in accordance with an embodiment.

FIG. 8 is a flowchart of a method of forming the arrangement shown in FIG. 5, using an example process having boro-silicate glass tubes as the X-ray transparent material and tungsten as the X-ray opaque material. As is well known, a glass tube subjected to a proper amount of heat and drawing pressure may be reduced from an original diameter to a selected smaller diameter, which is accompanied by increasing tube length in proportion to the reduction in width. By repetition of the heat drawing process a capillary tube of desired dimensions may be obtained. By bundling parallel lengths of the capillary tubes together and thermally fusing the glass walls of the tubes together, arrays of capillary tubes may be formed in many desired shapes, such as blocks or plates. The plates may be formed from the blocks by separating selected length sections from the block perpendicular to the direction of the capillary tubes.

At step 802 a block of capillary tubes is formed having the desired dimensions, for example as shown in FIGS. 1 through 4. This step includes the heat forming of the boro-silicate glass tubes into capillary tubes having the correct dimensions, forming a block having a desired shape by parallel placement of a set of capillary tubes, and heat fusing the capillary tubes into a single block of X-ray transparent material having a set of cylindrical holes.

At step 804 the block is separated into plates having a selected thickness, where the set of cylindrical holes pass through a thinnest plate thickness. The plates may be separated from the block by cutting, sawing, laser, or other known methods. Sawing may include using a wire saw, a radius saw, or other methods. Step 804 produces a plate having open ended tubes extending through the plate thickness. The ends of the tubes may be ground or polished to remove excessively rough surfaces and glass defects by use of grinding wheels, polishing wheels, chemical mechanical polishing (CMP), or other methods known in the art. In an embodiment, the plates have a thickness that determines the length of the capillary tubes L, where L is at least 50 times larger than an inside diameter of the capillary tubes. In the finished X-ray anti-scatter device this ratio increases the number of undesirable off-axis X-rays that reach the X-ray imaging device.

At step 806 a layer of X-ray opaque material, such as tungsten (W) or a composite layer including tungsten, is formed inside each of the capillary tubes. The tungsten layer should have a thickness sufficient to block a majority of incident X-rays having a selected energy, or less. The tungsten layer should coat essentially the entire length L of the capillary tubes with the desired thickness. The coating of long narrow tubes having aspect ratios of 50 to 1, or greater, as described with reference to the capillary tubes of step 804, may require the use of Atomic Layer Deposition (ALD) methods, or Chemical Vapor Deposition (CVD) methods that have growth characteristics and features in common with ALD methods. ALD methods of layer deposition are known, as are CVD methods that incorporate some ALD features. ALD methods are known to provide very controllable thickness and composition layers, which have highly conformal layer characteristics in areas having high aspect ratios. The high aspect ratio coverage possible using ALD methods may be useful for X-ray anti-scatter devices, since high aspect ratios result in better image quality. However, ALD is a slow and expensive method of layer deposition.

It is also known that metals, such as tungsten, have a coefficient of thermal expansion (CTE) that is much greater than found in dielectric materials, such as boro-silicate glass or plastic. A layer of tungsten in a boro-silicate glass tube subjected to thermal cycling may delaminate or form flakes of tungsten, either of which may damage the efficiency of the X-ray anti-scatter device. It would be desirable to provide an X-ray opaque layer that has a CTE that is closer to the CTE of glass, or a layer that has thermal stress relief layers.

In an embodiment, the X-ray opaque layer includes a first layer directly on the glass that consists of aluminum oxide having a first thickness. A second layer formed on the first layer consists of tungsten having a second thickness. Subsequent alternating layers of aluminum oxide and tungsten having selected thicknesses form a composite layer having an overall thickness sufficient to block most X-rays of less than a selected energy. The composite layer may have a composition that grades smoothly from essentially entirely aluminum oxide near the glass tube, to essentially entirely tungsten as the distance from the glass increases. The composition may be varied by adjusting the thickness of the aluminum oxide and tungsten layers in the composite layer.

At step 808 the tungsten layer that may have formed on the block outside of the capillary tubes may be removed. While it is important that the X-ray transparent channels are clear, an X-ray opaque coating on the face of the plate will reduce the total number of X-rays that reach the imaging system, whether or not the X-rays are on or off-axis. This may require an increase in the total number of X-rays produced for a given image and increase X-ray exposure time and cost. If the excess X-ray opaque material is not a problem, then step 808 may be deleted and the process goes to step 810.

At step 810 the finished flat plate forming an X-ray anti-scatter device may be formed into a focused device such as shown in FIG. 6 or FIG. 7 if desired. The use of focused devices allows greater aspect ratios for the X-ray transparent channels to be used, which results in better image quality. This is because in a device having parallel anti-scatter tubes such as shown in FIG. 5, only the tubes in the center directly facing the X-ray source will have the on-axis X-rays travel exactly parallel to the tube axis. Therefore, as the distance from the center of the plate increases the number of on-axis X-rays that hit the sides of the tubes and are absorbed increases, and the image strength is reduced unnecessarily. This may be a problem with X-ray anti-scatter devices that are either very large, such as would be used in a whole chest X-ray procedure, or are very close to the X-ray source. However, for X-rays on small areas, such as a finger or a hand, the use of flat X-ray anti-scatter devices may be desired for the reduced cost and ease of handling. For small area X-ray anti-scatter devices this step may be deleted and the process goes to the end at step 812.

Figure 9:
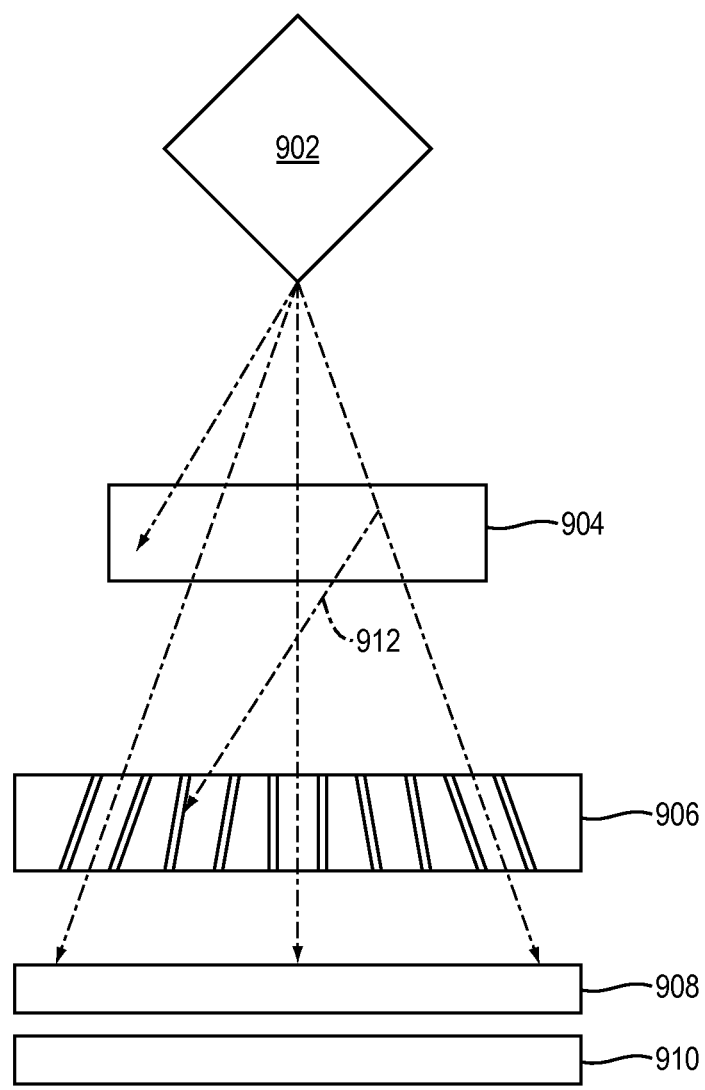
FIG. 9 is a schematic of an imaging system using an X-ray anti-scatter device, in accordance with some embodiments.

FIG. 9 is a schematic of an imaging system using an X-ray anti-scatter grid, in accordance with some embodiments described herein. The X-ray imaging system includes an X-ray source 902 that generates X-rays having a desired energy that may depend upon the thickness and density of the object to be examined 904. The X-rays travel in straight lines as shown by representative rays shown by the dashed arrows. The object to be examined 904 may be a patient having a chest X-ray, or the engine block of an internal combustion engine, or any of many other objects that may require an internal image.

X-rays that pass directly thru the object 904 are passed thru the X-ray anti-scatter device 906, and imaged at the X-ray detector. X-rays that are deflected, such as the dashed arrow labeled 912, are too far off-axis to pass thru the X-ray anti-scatter device 906, and are absorbed by the X-ray opaque layer.

The X-ray detector 908 may be a scintillating material 908 that emits visible light when absorbing an X-ray. The visible light may then be detected and recorded as an image by the imager 910, which may be a CMOS imager, a CCD imager, photo sensitive film or other well-known optical imagers. Alternatively, the detector 908 and the imager 910 may be replaced by X-ray sensitive film.

In an embodiment, the X-ray imaging system includes the X-ray anti-scatter device 906 directly attached to the scintillator 908, which is attached to the imager 910 in an integrated package. This improves the ease of use of the X-ray imaging system and is not practical with known X-ray anti-scatter devices, which are too bulky and heavy to integrate with the detectors.

The disclosed X-ray anti-scatter device improves image resolution over the prior art, and reduces the cost and weight of prior art devices. The reduced thickness of the X-ray opaque layers made possible by the disclosed methods reduces what are known as image artifacts due to the thickness of the prior art lead sheet X-ray opaque layers. The artifact problem is addressed in the prior art by mechanisms that slowly move the X-ray anti-scatter grid randomly during the course of the X-ray exposure.

While various embodiments of the invention have been particularly shown and described, it will be understood by those skilled in the art that various changes in form and details may be made therein without departing from the spirit and scope of the invention as defined by the appended claims.

What is claimed is:

1. An X-ray anti-scatter device, comprising:
   an X-ray transparent dielectric material having a first lateral extent in a first direction, a second lateral extent in a second direction orthogonal to the first direction, the first and second directions defining a plane, the X-ray transparent dielectric material having a thickness orthogonal to the plane; and
   a set of X-ray opaque tubes extending at least partially through the X-ray transparent dielectric material, each of the X-ray opaque tubes having a selected axial orientation, a selected outside width and a selected inside width;
   wherein the X-ray opaque tubes comprise tungsten and the X-ray transparent dielectric material comprises at least one of borosilicate glass and anodic aluminum oxide.

2. The X-ray anti-scatter device of claim 1, wherein the thickness of the X-ray transparent dielectric material is substantially uniform across the first and second lateral extents.

3. The X-ray anti-scatter device of claim 2, wherein the set of X-ray opaque tubes extends substantially entirely through the plane.

4. The X-ray anti-scatter device of claim 2, wherein the set of X-ray opaque tubes have a cross sectional shape including at least one of circular, elliptical, oval, hexagonal and polygonal.

5. The X-ray anti-scatter device of claim 1, wherein the selected outside width and the selected inside width of each of the X-ray opaque tubes are selected to obtain an X-ray open area ratio of greater than 80%.

6. The X-ray anti-scatter device of claim 1, wherein the selected inside width of the X-ray opaque tubes and the thickness of the X-ray transparent dielectric material are selected to obtain a thickness to width ratio of greater than 100/1.

7. The X-ray anti-scatter device of claim 6, wherein the X-ray opaque tubes are straight and hollow.

8. The X-ray anti-scatter device of claim 1, wherein the tungsten comprises a conformal layer on an inside surface of a hollow capillary tube, and extends substantially an entire length of the hollow capillary tube.

9. The X-ray anti-scatter device of claim 1, wherein the selected axial orientation for each individual one of the set of X-ray opaque tubes is substantially directed towards a point a selected distance from the plane of the X-ray anti-scatter device.

10. A method of forming an X-ray anti-scatter device, comprising:
forming a block from a set of parallel straight hollow capillary tubes, each hollow capillary tube comprising an X-ray transparent dielectric material having a selected inner diameter, a selected outer diameter, and a selected length;
opening a first end and a second end of substantially each one of the set of parallel straight hollow capillary tubes; and
forming an X-ray opaque material layer having a selected thickness on a surface of each one of the set of parallel straight hollow capillary tubes;
wherein forming the X-ray opaque material includes depositing a first layer having a selected layer thickness formed by a set of thin layers of a first material;
depositing a second layer having a selected layer thickness formed by a set of thin layers of a second material on the first layer; and
alternately depositing additional layers of the first material and the second material, each individual first and second material layer having a separate selected thickness, to form the X-ray opaque layer having a selected X-ray opaque material layer thickness and a selected composition.

11. The method of claim 10, wherein the first material is comprised substantially of alumina and the second material is comprised substantially of tungsten.

12. The method of claim 10, further including selecting each first material and second material layer thickness to provide a specified X-ray opaque material composition for each of a set of thickness locations in the X-ray opaque layer.

13. The method of claim 10, wherein forming the layer of the X-ray opaque material includes atomic layer deposition.

14. The method of claim 10, wherein forming the layer of the X-ray opaque material includes forming a layer having composition selected for thermal stress relief with the X-ray transparent dielectric material.

15. The method of claim 10, wherein forming the block further includes at least some of the straight hollow capillary tubes having an elliptical cross section.

16. The method of claim 10, further including modifying the block to direct one end of each one of the straight hollow capillary tubes towards a point at a selected distance from a center point of the block.

17. The method of claim 16, wherein modifying the block further includes forming a substantially circular curve having a selected radius of curvature from the block having the set of parallel straight hollow capillary tubes.

18. The method of claim 16, wherein modifying the block includes at least one of thermal flowing the X-ray transparent dielectric material over a form, and cutting slices from the block.

19. A system for forming X-ray images, comprising:
a source of X-rays;
an X-ray anti-scatter device including a set of straight X-ray transparent hollow tubes, each tube including an X-ray opaque layer inside the hollow tube and a longitudinal axis directed at the source of the X-rays; and
an X-ray detector attached to an X-ray imaging device;
wherein the source of X-rays provides X-rays having a selected energy;
and wherein the set of straight X-ray transparent hollow tubes comprise a borosilicate glass, and the X-ray opaque layer comprises a layer of tungsten having a thickness sufficient to block greater than 90% of X-rays from the source of X-rays.

20. The system of claim 19, wherein the X-ray imaging device comprises a scintillating material fixed adjacent to the X-ray anti-scatter device and a solid state imaging device fixed adjacent to the scintillating material.

21. The system of claim 19, wherein the X-ray anti-scatter device comprises a substantially flat plane having a substantially uniform thickness.

22. An X-ray anti-scatter device, comprising:
a set of straight hollow open ended tubes formed of an X-ray transparent dielectric material, each straight hollow open ended tube including a layer of X-ray opaque material covering an inside surface;
substantially all of the straight hollow open ended tubes aligned towards a selected point; and
the set of straight hollow open ended tubes physically connected to each other at one end of each tube to form a conic section curved surface;
wherein the thickness of the X-ray opaque material is selected to obtain an X-ray open area ratio of greater than 80% and an X-ray stopping power greater than 90% for X-rays under a selected energy.

23. The X-ray anti-scatter device of claim 22, wherein each one of the set of straight hollow open ended tubes have a circular cross section.

24. The X-ray anti-scatter device of claim 22, wherein the X-ray transparent dielectric material comprises borosilicate glass and the X-ray opaque tubes comprises tungsten.

* * * * *